US012806184B2

(12) United States Patent
Berlia et al.

(10) Patent No.: US 12,806,184 B2
(45) Date of Patent: Nov. 24, 2026

(54) STABLE PHARMACEUTICAL ORAL LIQUID FORMULATION OF AN ANTISPASMODIC AGENT

(71) Applicant: Drotastar LLC, Lewes, DE (US)

(72) Inventors: Sushma Paul Berlia, New Delhi (IN); Nishant Berlia, New Delhi (IN); Aditya Berlia, New Delhi (IN); Gurvinder Singh, New Delhi (IN)

(73) Assignee: Drotastar LLC, Lewes, DE (US)

( * ) Notice: Subject to any disclaimer, the term of this patent is extended or adjusted under 35 U.S.C. 154(b) by 444 days.

(21) Appl. No.: 18/361,080

(22) Filed: Jul. 28, 2023

(65) Prior Publication Data

US 2024/0091217 A1 Mar. 21, 2024

(30) Foreign Application Priority Data

Jul. 29, 2022 (IN) ............................ 202211043457

(51) Int. Cl.

*A61K 31/472* (2006.01)
*A61K 9/00* (2006.01)
*A61K 9/10* (2006.01)
*A61K 31/80* (2006.01)
*A61K 47/58* (2017.01)

(52) U.S. Cl.

CPC .......... *A61K 31/472* (2013.01); *A61K 9/0053* (2013.01); *A61K 9/10* (2013.01); *A61K 31/80* (2013.01); *A61K 47/585* (2017.08)

(58) Field of Classification Search

CPC .................................................... A61K 31/472

See application file for complete search history.

(56) References Cited

U.S. PATENT DOCUMENTS

| | | | |
|---|---|---|---|
| 5,154,926 | A | 10/1992 | Kawasaki et al. |
| 5,616,621 | A | 4/1997 | Popli et al. |
| 7,510,728 | B2 | 3/2009 | Koike |
| 9,132,096 | B1 | 9/2015 | Rekhi et al. |
| 2005/0181050 | A1 | 8/2005 | Hirsh et al. |
| 2006/0079514 | A1 | 4/2006 | Preston |
| 2006/0172005 | A1 | 8/2006 | Hara et al. |
| 2009/0136569 | A1 | 5/2009 | Uemura et al. |
| 2009/0311321 | A1 | 12/2009 | Mimura et al. |
| 2010/0166858 | A1 | 7/2010 | Mehta et al. |
| 2010/0215740 | A1 | 8/2010 | Pilgaonkar et al. |
| 2013/0017262 | A1 | 1/2013 | Mullen et al. |
| 2014/0080864 | A1* | 3/2014 | Badabhagni ......... A61K 31/485 514/307 |
| 2014/0147501 | A1 | 5/2014 | Van Lengerich et al. |
| 2015/0024059 | A1 | 1/2015 | Mehta et al. |
| 2018/0325907 | A1 | 11/2018 | Wang et al. |
| 2022/0040196 | A1 | 2/2022 | Nandi et al. |

FOREIGN PATENT DOCUMENTS

| | | | |
|---|---|---|---|
| CN | 101288645 | A | 10/2008 |
| CN | 102149382 | A | 8/2011 |
| EP | 1025858 | A1 | 8/2000 |
| EP | 1200088 | A2 | 5/2002 |
| EP | 2268282 | B1 | 10/2014 |
| EP | 2808013 | | 12/2014 |
| EP | 2808013 | A1 | 12/2014 |
| EP | 2709599 | B1 | 12/2017 |
| EP | 3520781 | A1 | 8/2019 |
| IN | 2006 | | 2/2008 |
| IN | 2006DE01625 | A | 2/2008 |
| IN | 2013 | | 6/2015 |
| IN | 2013MU02208 | A | 6/2015 |
| IN | 2014 | | 8/2016 |
| IN | 2014CH05678 | A | 8/2016 |
| RU | 2535049 | C1 | 12/2014 |
| RU | 2729659 | C1 | 8/2020 |
| WO | 1999004822 | A2 | 2/1999 |
| WO | 2000021504 | A1 | 4/2000 |
| WO | 2007019888 | A2 | 2/2007 |
| WO | 2011080716 | A2 | 7/2011 |
| WO | 2012159964 | A1 | 11/2012 |
| WO | 2016041036 | A1 | 3/2016 |
| WO | 2016075617 | A1 | 5/2016 |
| WO | 2018100413 | A1 | 6/2018 |
| WO | 2019075127 | A1 | 4/2019 |
| WO | 2019149917 | A1 | 8/2019 |
| WO | 2021181262 | A1 | 9/2021 |
| WO | 2024023785 | A1 | 1/2024 |

OTHER PUBLICATIONS

Blasko (1998) "Pharmacology, mechanism of action and clinical significance of a convenient antispasmodic agent: Drotaverine", J Am Med Assoc Ind. Physicians' Update 1998, 6:63-70.
Bolaji et al. (1996) "Pharmacokinetics and bioavailability of Drotaverine in humans", Eur J Drug Metab Pharmacokinet., 21(3):217-221.
Anonymous (2019) "Kyron—Corel Pharma Chem", XP93100416, Retrieved from the Internet: URL: https://web.archive.org/web/20191029140722/https://www.corelpharmachem.com/products/kyron/ [retrieved on Nov. 10, 2023].
Blasko (1998), "Pharmacology, mechanism of action and clinical significance of a convenient antispasmodic agent: Drotaverine", J Am Med Assoc Ind. Physicians' Update, 6:63-70.
Bolaji et al. (1996), "Pharmacokinetics and bioavailability of Drotaverine in humans", Eur J Drug Metab Pharmacokinet., 21(3):217-221.4.
Der Pharmacia Lettre et al. (2010) "Design and evaluation of taste masked Drotaverine HCI orodispersible tablets using polymethacrylate polymers", Der Pharmacia Lettre, Jan. 1, 2010 (Jan. 1, 2010), pp. 223-231, XP055160051, Retrieved from the Internet: URL:http://scholarsresearchlibrary.com/DPL -vol. 2-iss6/DPL-2010-2-6-223-231.pdf [retrieved on Jan. 5, 2015].
Dipasquale et al. (2018) "Gastrointestinal symptoms in children: Primary care and specialist interface", International Journal of Clinical Practice, Medicon International, Esher, GB, vol. 72, No. 6 (9 pages).
El-Nabarawi (2019) "Effect of Co-Process Excipients in Formulation Of ODTs Using a Model Drug", International Journal of Pharmaceutical Sciences and Research, 10(5), XP093076759.

(Continued)

*Primary Examiner* — Rei Tsang Shiao

(74) *Attorney, Agent, or Firm* — Finnegan, Henderson, Farabow, Garrett & Dunner, LLP

(57) ABSTRACT

The present disclosure provides oral suspension formulations of drotaverine or a salt thereof, methods of their preparation, and their use in treatment.

27 Claims, No Drawings

(56) References Cited

OTHER PUBLICATIONS

Hari et al. (2018) "Preparation and Evaluation of Drotaverine Hcl Oral Disintegrating Tablets Using Solid Mixture Technique", Asian J Pharm Clin Res, 11(6): 289-297.
International Patent Application No. PCT/IB2021/051942, filed Mar. 9, 2021, by Almendro Properties and Trading LLP, International Search Report and Written Opinion of International Searching Authority, mailed Jun. 15, 2021.
International Patent Application No. PCT/IB2023/051167, filed Feb. 9, 2023, by Sushma Paul Berlia, International Search Report and Written Opinion of International Searching Authority, mailed Jun. 22, 2023.
International Patent Application No. PCT/IB2023/057693, filed Jul. 28, 2023, by Sushma Paul Berlia, International Search Report and Written Opinion of International Searching Authority, mailed Nov. 29, 2023.
International Patent Application No. PCT/IB2023/057694, filed Jul. 28, 2023, by Sushma Paul Berlia, International Search Report and Written Opinion of International Searching Authority, mailed Nov. 23, 2023.
International Patent Application No. PCT/US2025/036945, filed Jul. 9, 2025, by Drotastar Llc, International Search Report and Written Opinion of International Searching Authority, mailed Nov. 18, 2025.
Kunal et al. (2019) "Formulation and Evaluation of Floating Matrix Tablets of Drotaverine Hydrochloride", Journal of Drug Delivery and Therapies, 9(3):200-206.
Kuralla et al. (2018) "Preparation and evaluation of drotaverine hydrochloride orally disintegrating tablets using melt granulation", J Applied Pharm Sci. 8(10):39-46.
Linakis et al. (2016) "Challenges Associated with Route of Administration in Neonatal Drug Delivery", Clinical Pharmacokinetics, 55(2):185-196.
Maone et al. (1990) "A New Method for Delivering a Taste without Fluids to Preterm and Term Infants", Dev. Psychobiol., 23(2):179-191.
Narang et al. (2015) "Efficacy and safety of drotaverine hydrochloride in children with recurrent abdominal pain: A randomized placebo controlled trial", Indian Pediatrics, Springer India, New Delhi, 52(10):847-851.
Prabhu et al. (2007) "Studies on taste masking of Drotaverine hydrochloride and its formulation", Indian Drugs, Indian Drug Manufacturers' Association, In, 44(11), XP009549391.
Prajapati et al. (2015) "Formulation and Evaluation of Orodispersible Tablets of Drotaverine Hcl", International Journal of Current Research in Pharmacy, 1(1):60-71, XP093098095.
Prakash et al. (2013) "Formulation and Evaluation of Floating Drotaverine Hydrochloride Tablets Using Factorial Design", Res J Pharm, Bio and Chem Sci, 4(4):546-555.
Samet et al. (1976) "The Evaluation of Bellergal Tablets Compared to Librium and Placebo in the Treatment of Symptoms of Anxiety Tension States Associated with Functional Gastrointestinal Disorders", Psychosomatics, 17 (4):202-209.
Sikandar et al. (2011) "Taste Making: an Important Pharmaceutical Technology for the Improvement of Organoleptic Property of Pharmaceutical Active Agents", Eur. J. Biol. Sci. 3(3):67-71.
Strickley et al. (2008) "Pediatric drugs-a review of commercially available oral formulations", Journal of Pharmaceutical Sciences, 97(5):1731-1774, XP055121290.
Tranova et al. (2021) "Study of rheological and tableting properties of lubricated mixtures of co-processed dry binders for orally disintegrating tablets", European Journal of Pharmaceutical Sciences, Elsevier Amsterdam, NL, vol. 168, XP086895284.
Zhu et al. (2017) "Efficacy and safety of combination therapy with Drotaverine and ketorolac versus ketorolac monotherapy for acute renal colic: A retrospective study of 322 patients", International Journal of Clinical and Experimental Medicine, 10(2):3454-3461.

* cited by examiner

STABLE PHARMACEUTICAL ORAL LIQUID FORMULATION OF AN ANTISPASMODIC AGENT

FIELD

The present disclosure relates to a stable pharmaceutical oral suspension formulation of an antispasmodic agent. More particularly, the disclosure relates to stable pharmaceutical oral suspension formulations of Drotaverine or a salt thereof. The disclosure also relates to methods for preparation of such formulations and uses thereof.

BACKGROUND

Oral route of administration for drugs is preferred in pediatric patients. Unlike in adults, where oral solid dosage forms such as tablets or capsules will be acceptable to the majority of patients, pediatric patients that include neonates, newborns, toddlers, and young children are unable to swallow conventional tablets. They prefer very small volumes of doses of medicine to avoid volume overload. Therefore, oral suspension dosage forms such as a suspension administered as drops are considered to be a suitable formulation for infants and very young children. Drops from an oral suspension provide delivery of small volumes, delivery of low doses of a drug, ease of swallowing, and dosing flexibility.

Development of age-appropriate medicines for infants and children involves not only understanding their preferences for different formulations, flavors, and textures of products, but also understanding the physical and biochemical differences between children and adults. The design of a pediatric formulation may take into account factors such as ensuring a minimal impact on the lifestyle of the child, administering a low dosage frequency, providing a palatable dosage form, allowing individualized dosing or dose banding for effective therapy, providing sufficient bioavailability, avoiding toxic excipients, providing a convenient and reliable route of administration, and using a robust production process with minimal cost.

Taste is an important and critical parameter in administering oral formulations. Babies are born with sensitive taste and may even have more widely distributed taste buds than adults. Newborns are capable of distinguishing between sweet and bitter flavors with taste buds on the back of their tonsils, throat, and tongue. Newborns typically prefer sweet tastes like breastmilk. Several lines of evidence indicate that the liking for sweet taste is inborn. T. R. Maone et al., *A New Method for Delivering a Taste without Fluids to Preterm and Term Infant,* 23 Dev., Psychobiol., 179 (1990). Bitter is often considered the opposite of sweet taste and typically is considered bad and undesirable. Many drugs are naturally bitter, and bitterness is one of the problem encountered during drug formulation development. The bitter taste of a drug can cause patients (especially infants and children) to be unwilling or unable to swallow such formulations.

Simple taste-masking is sometimes insufficient to hide a drug's bitter flavor and more complex formulations are required. Excipients are typically used to improve palatability, shelf-life, and/or improve the manufacturing processes. Many excipients are known to be harmful to neonates, so the selection of excipients in neonatal medications is another important factor to be monitored. Though excipients are generally considered "inactive ingredients," many excipients that are pharmacologically inert in adults may be toxic in neonates and children. For example, use of small quantities of ethanol as a solvent in formulations such as diazepam oral solution is not an issue for adults but can lead to CNS (central nervous system) depression in neonates, thereby rendering it inappropriate for use in that population. Further, inclusion of propylene glycol in formulations used in neonates (such as cetirizine oral solution) has raised concerns for ototoxicity and CNS toxicity in past (Linakis et al., 2016; Clinical Pharmacokinetics, volume 55, pages 185 196). Thus, certain excipients, for example, ethanol, propylene glycol, benzyl alcohol and parabens, can retard ongoing organ development in neonates and children and are not recommended. Excipients used in the development of a product need to be safe and acceptable for use in neonates and children.

In infants and young children, abdominal pain is a common problem and can be a difficult symptom to treat. While causes of pain are diverse, abdominal pain occurs in newborns up to adulthood. Segregating this population by age groups of 0-1, 1-6, 6-11, and 11-18 years of age helps in diagnosis and designing appropriate formulations for treatment of pain. Owing to the wide age range of the pediatric population, it is unlikely that a single formulation will be appropriate across the 18-year range, which may result in multiple products. While older children from 6 to 11 or 11 to 18 years old can be administered solid oral dosage forms, infants and children below 6 years cannot easily swallow solid oral dosage forms. In their age groups a liquid oral formulation can provide accurate dose titration with ease of administration.

Drotaverine HCl is a benzylisoquinoline derivative and is an analogue of papaverine. Its chemical name is 1-[(3,4-diethoxy phenyl) methylene]-6,7-diethoxy-1,2,3,4-tetrahydroisoquinoline with a molecular formula of $C_{24}H_{31}NO_4 \cdot HCl$.

Drotaverine is a highly potent spasmolytic agent directly acting on smooth muscles and devoid of anticholinergic side effects. It is used in the treatment of various gastrointestinal diseases, biliary dyskinesia, and vasomotor disease associated with smooth muscle spasms. Drotaverine is adsorbed on cell surface and alters the cell membrane potential and permeability. It has a dual mechanism of action by inhibiting enzyme phosphodiesterase IV (PDE IV) and calmodulin (CAM), which is a calcium binding protein. This causes an increase in cyclic adenosine monophosphate (cAMP) levels in smooth muscles, thereby decreasing the concentration of free calcium ions ($Ca^{2+}$). The decrease in $Ca^{2+}$ ions along with the inhibition of calmodulin leads to inhibition of "Calmodulin-Calcium complex" (CAM-Ca2+) formation. This process inhibits myosin light chain kinase enzyme (MLCK), leading to dephosphorylation of actomyosin phosphate complex and relaxation of smooth muscles.

Some pharmacokinetic parameters of Drotaverine, such as elimination, half-life, plasma clearance, renal clearance, and apparent volume of distribution, may not be influenced by the route of drug administration. The pharmacokinetic parameters for immediate release (IR) Drotaverine tablets (80 mg) have been studied. [O. O. Bolaji et al., *Pharmacokinetics and Bioavailability of Drotaverine in Humans,* 21 Eur. J. Drug Metab. Pharmacokinet. 217 (1996)]. The drug is mainly eliminated by non-renal routes since renal clearance accounted for only 0.31+/−0.13% of the total plasma clearance. Absolute bioavailability was variable and subject dependent and ranged between 24.5-91% with a mean of 58.2+/−18.2% (mean+/−SD). It is suggested that the high variation in bioavailability of Drotaverine HCl after oral administration results in significant inter-individual differences in therapeutic response to the drug. In pharmacokinetic and bioavailability studies, Drotaverine has shown rapid absorption viz., onset of action within 12 minutes after oral administration of 80 mg strength IR tablets. Peak plasma levels occurred after 1 to 3 hours, while elimination half-life ranged from 7 to 11.95 hours. Drotaverine is considered to be very safe in toxicological studies, as the reported oral LD50 for Drotaverine is >1000 mg/Kg body weight, and therefore has a wide therapeutic index.

Currently, Drotaverine is available as a conventional IR tablet, in strengths of 40 mg and 80 mg tablets used to relieve and prevent smooth muscle spasm of various organs regardless of their function and innervation. The approved daily doses of Drotaverine tablet are 120-240 mg (in 2-3 divided doses) in adults, 80 to 200 mg (in 2 to 5 divided doses) in children 6-18 years old, and 40 to 120 mg (in 2 to 3 divided doses) in children between 1 to 6 years old. In children, oral suspension of Drotaverine is also used for the treatment of abdominal pain. It is available in two different strengths, 10 mg/5 mL and 20 mg/5 mL. The dosage of Drotaverine suspension is 0.5 mL/kg or 1 mL/kg body weight. TID up to 120 mg/day in children between 1 to 6 years of age and 0.5 mL/kg or 1 mL/kg body weight TID up to 200 mg/day in children between 6 to 12 years of age. The currently marketed strengths of Drotaverine suspension (10 mg or 20 mg per 5 mL) cannot be easily administered to infants and children below 3 years of age because of the large volumes per dosage unit. Hence, there is a need to develop suitable concentrated form of Drotaverine formulation which can be easily administered with reduced volume, preferably up to 1 mL in the form of oral suspension or spray.

Drotaverine contributes very effectively either alone or in combinations in relieving painful spasms from a wide variety of gastroenterological, urological, gynecological, and/or obstetrical diseases, and is the first drug of choice in emergency medicine in abdominal pain relief.

Drotaverine suspension can be administered to treat acute abdominal pain in children. Children usually have a poor sense of disease onset, location of pain, and are not able to effectively describe or vocalize the character, severity, duration, or radiation of pain, which are very important for diagnosis. For example, a child may not be able to describe the type of pain arising out of acute appendicitis, which is very common in children. As a PDE IV inhibitor, Drotaverine can be used to selectively relieve muscular abdominal pain while not masking the symptoms of other acute abdominal pain. This feature of Drotaverine makes it unique as compared with other existing anti spasmodic/anticholinergic drugs.

Drotaverine has demonstrated abdominal pain relief without side effects associated with anticholinergics. It is an effective and safe pharmaceutical agent in the management of recurrent abdominal pain during childhood. It is most commonly known to be used for alimentary tract problems in preschool- and school-aged children. Drotaverine is non-toxic, has minimal side-effects, and can be administered to children without long-lasting problems.

Irritable bowel syndrome (IBS) is often associated with flatulence, which causes pain and discomfort to the patient. In some embodiments, anti-flatulent active ingredients are useful in the treatment of conditions where retention of gas is problematic, such as excessive swallowing of air by infants, colicky pain, eating certain foods, functional dyspepsia, postoperative gaseous distension, peptic ulcers, spastic or irritable colon, or diverticulosis. Infants have an immature digestive system and swallowing air while crying or during feeding can cause gas or flatulence. Tiny bubbles of air form in the stomach or intestines, causing colicky pain. Some known anti-flatulents are simethicone and or activated dimethicone, which are indicated for relief of flatulence and abdominal discomfort due to excess gastrointestinal gas. Simethicone and activated dimethicone reduce the surface tension of small gas bubbles, and the over-the-counter (OTC) indication for these active agents is "for the relief of painful bloating, and the sensation of pressure and fullness, commonly referred to as gas in the digestive tract."

Simethicone and activated dimethicone are gastrointestinal protective agents with antifoaming action. They reduce surface tension of gas bubbles, forming larger bubbles that burst to release the gas. Released gas is either absorbed or eliminated naturally. Simethicone and activated dimethicone do not reduce the quantity of gas in the digestive tract; it only increases the rate at which it exits the body, without any effect on motility, secretion, and tonicity of the intestine. Simethicone is not absorbed by the body into the bloodstream and is therefore considered relatively safe.

Drotaverine has an extremely unpleasant bitter and lingering after taste. The source of bitterness is unknown. In some embodiments, masking the bitter taste of Drotaverine is extremely important to ensure patient compliance. Further, Drotaverine HCl is highly susceptible to oxidation and pH, which leads to chemical instability. Although a number of techniques have been tried so far to mask the taste of Drotaverine HCl without compromising the stability by using approaches like solid dispersion, drug coatings, or complexation with polymers, a palatable, stable, oral Drotaverine suspension, has not been reported in literature to date.

The Applicant's patent application WO2021181262A1 discloses controlled release tablet formulations of Drotaverine or salt thereof.

U.S. Pat. No. 5,154,926A discloses reduction of bitter taste of acetaminophen syrup by using a water-soluble macromolecule with a polyhydric alcohol and/or polymer of a polyhydric alcohol of molecular weight of 300 to 400. EP1025858A1 discloses relief of bitterness of basic drugs by combining propylene glycol with Povidone and/or copolyvidone.

WO/2019/075127 discloses a stable, oral liquid formulation of midodrine comprising midodrine and sucralose. EP2268282B1 discloses an oral pharmaceutical liquid formulation comprising deferiprone and a taste masking composition comprising an effective amount of a sweetener such as sucralose, thickening and suspension aid (for example hydroxyethylcellulose), humectant (such as glycerin) and at least one flavoring agent. However, sucralose is an artificial sweetener and its usage is prohibited for infants and children below 6 years of age.

U.S. Pat. No. 5,616,621A discloses a pharmaceutically acceptable taste masking liquid excipient base for administration of a relatively large amount of unpleasant tasting medicines. The patent document discloses that the taste masking effect is produced by increasing viscosity of the liquid excipient base by adding to the liquid excipient base a viscosity increasing amount of a combination of a normally solid polyethylene glycol and sodium carboxymethyl cellulose. Hari et al., 2018 (Asian J Pharm Clin Res, Vol 11, Issue 6, 2018, 289-297) discloses formulation of orally disintegrating taste masked tablets of Drotaverine HCl using solid mixture technique. The document discloses preparation of taste masked drug-polymer solid mixtures of Drotaverine HCl by using hydroxypropyl methylcellulose (HPMC) 3 cps and Rxcipient® FM1000/calcium silicate (Rxcipient®) as carriers using varying drug-polymer ratios of 1:1, 1:5, 1:7.5, and 1:9. Increase in viscosity is assumed to limit contact of drug with tongue, thereby avoiding dilution and dissolution of the taste-offending ingested medication by saliva. However, this approach is only moderately successful in reducing bitterness especially at high drug loading. Though the approach may reduce bitterness at the onset, bitter aftertaste becomes prominent after swallowing because thick preparations are more difficult to wash down thus leaving behind some residual viscous liquid medicament in mouth after swallowing for long time. Further, water intake to avoid bitter aftertaste reduces viscosity and results in dilution of residual liquid medicament and subsequent dissolution of the drug in the mouth.

Preparation of dosage forms using drug-loaded ion exchange resins is known in the field of art. CN101288645A discloses a tilidine (analgesic) drug-resin oral suspension and a preparation method thereof. US20050181050A1 discloses modified release liquids containing drug-loaded ion exchange resin particles. Regulatory authorities require removal of such solvents from pharmaceutical products before ingestion. US20100166858A1 discloses a coated drug-ion exchange resin complex comprising a core composed of a drug-ion exchange resin complex in a mixture with a release retardant. The coating disclosed in the patent document is a polyvinyl acetate polymer and a plasticizer. The process disclosed in the document employs complex and lengthy steps and use of potentially harmful agents for children.

To date, no concentrated oral suspension formulation of Drotaverine or salt thereof that is palatable, safe, and stable is available for neonates, infants, and children below 3 years of age.

Various approaches to mask the bitter taste of drugs use one or more different flavoring methodologies. However, approaches effective in masking the taste of a particular bitter drug often do not apply to another drug.

Oral suspensions are considered to be suitable formulations particularly in infants and in very young children. Oral suspensions administered as drops provide a mechanism to deliver small volumes or low doses of a drug along with other advantages such as ease of swallowing and dosing flexibility. However, Drotaverine HCl degrades extensively in alkaline medium, higher oxidative stress conditions, and in the presence of light. Hence, there is a need to develop a chemically stable palatable suspension formulation of Drotaverine or salt thereof with advantages of accurate dose titration, ease of administration, and dosing flexibility. In some embodiments, the present disclosure aims to provide oral suspension formulations that facilitate administration of a range of doses suitable for infants and children below 3 years of age. Further, in some embodiments, the formulations should be devoid of harmful excipients and should have longer shelf life. Despite of all the efforts made to date, a need remains for stable and palatable pharmaceutical oral suspension formulations of an antispasmodic agent.

SUMMARY

In some embodiments, the present disclosure provides for an oral suspension comprising Drotaverine or a salt thereof, wherein the Drotaverine or salt thereof is in a concentration of greater than 4 mg/mL. In some embodiments, the suspension comprises 5-30 mg/mL Drotaverine or salt thereof. In some embodiments, the suspension comprises a Drotaverine-resin complex, wherein the ratio of Drotaverine to resin is 1:2 to 1:6. In some embodiments, the Drotaverine-resin complex comprises granules, wherein the size of the granules are in the range of 300 microns to 150 microns. In some embodiments, the resin is selected from Kyron 114, Kyron 314, Indion 204, Indion 234, Indion 294, or a combination thereof.

In some embodiments, the present disclosure provides for an oral suspension comprising Drotaverine or a salt thereof and an anti-flatulent agent. In some embodiments, the anti-flatulent agent is simethicone or activated dimethicone. In some embodiments, the suspension comprises 10-80 mg/mL simethicone or activated dimethicone.

In some embodiments, the present disclosure provides for an oral suspension of Drotaverine or a salt thereof comprising a water-soluble polymer. In some embodiments the water-soluble polymer comprises a hydroxypropyl methylcellulose, a polyvinylpyrrolidone, gelatin, a soluble starch, or a combination thereof. In some embodiments, the oral suspension comprises a solvent comprising a sugar alcohol, a polyhydric alcohol, or a combination thereof. In some embodiments, the sugar alcohol is sorbitol or sorbitol (70% liquid). In some embodiments, the polyhydric alcohol is glycerin. In some embodiments, the solvent comprises a combination of sorbitol (70% liquid) and glycerin in a ratio of 1:1 to 9:1. In some embodiments, the oral suspension comprises a suspending agent comprising sodium carboxymethylcellulose (Sod CMC), xanthan gum, or a combination thereof. In some embodiments, the suspending agent is in an amount of 0.05% to 3.0% w/w. In some embodiments the suspension comprises a sweetener. In some embodiments, the sweetener is an artificial sweetener comprising aspartame, sodium saccharin, acesulfame K, sucralose, or a combination thereof. In some embodiments, the sweetener is a natural sweetener comprising sucrose, sorbitol, or a combination thereof. In some embodiments, the suspension comprises a flavorant, a colorant, an antioxidant, a chelating agent, a surfactant, a wetting agent, a pH modifier, an acidifier, a preservative, a solvent, or a combination thereof. In some embodiments, the antioxidant is in an amount of 0.05% to 4.0% w/w. In some embodiments, the suspension exhibits dosage uniformity, uniform dispersibility and re-dispersibility as measured by High-Performance Liquid Chromatography (HPLC).

In some embodiments, the present disclosure provides for an oral suspension of Drotaverine or a salt thereof that is stable for three months when stored at 25-30° C. and 60-75% relative humidity (RH) as long-term storage conditions. In some embodiments, the suspension is stable for six months when stored at 25-30° C. and 60-75% RH as long term storage conditions. In some embodiments, the suspension is stable for 2 years when stored at 25-30° C. and 60-75% RH as long-term storage conditions. In some embodiments, the suspension is stable for three months when stored at 40° C. and 75% RH as long-term storage conditions. In some embodiments, the suspension is stable for six months when stored at 40° C. and 75% RH as long-term storage conditions.

In some embodiments, the present disclosure provides for an oral suspension of Drotaverine or a salt thereof that exhibits improved taste, improved aftertaste, improved palatability, or a combination thereof.

In some embodiments, the present disclosure provides for a method of preparing an oral suspension of Drotaverine or salt thereof comprising: (a) heating a quantity of water and adding at least one preservative and milled sucrose, stirring the resulting mixture continuously until dissolved to obtain a solution; (b) cooling the solution to obtain a cooled solution; (c) adding at least one acidifier and at least one antioxidant into the cooled solution until dissolved to obtain a solution; (d) adding at least one wetting agent into the solution until dissolved to obtain a solution; (e) adding at least one stabilizer and a dispersion that has been obtained by soaking at least one suspending agent in water, until dissolved to obtain a bulk solution; (f) sifting a drug-resin complex comprising Drotaverine or a salt thereof through a sieve, adding the bulk solution obtained in step (e), and stirring until dissolved to obtain a bulk suspension; and (g) adding a quantity of water to the bulk suspension to obtain a suspension of Drotaverine or a salt thereof. In some embodiments, the method comprises adding simethicone or activated dimethicone with Drotaverine in step (f). In some embodiments, the drug-resin complex comprises Kyron 114, Kyron 314, Indion 204, Indion 234, or Indion 294, or a combination thereof.

In some embodiments, the drug-resin complex comprising Drotaverine or a salt thereof are mixed in a ratio of 1:2 to 1:6. In some embodiments, the drug-resin complex is air dried or dried using drying equipment. In some embodiments, the dried drug-resin complex has less than 5.0% w/w of water. In some embodiments, the sieve used in step (f) comprises a mesh, wherein the mesh is no larger than 300 microns.

In some embodiments, the present disclosure provides for a method of treating abdominal pain comprising administering to a subject in need thereof an oral dosage form comprising Drotaverine or a salt thereof and Simethicone.

In some embodiments, the present disclosure provides for the use of a liquid dosage form comprising Drotaverine or a salt thereof and Simethicone to treat abdominal pain comprising administering the liquid dosage form to a subject in need thereof.

DETAILED DESCRIPTION

In some embodiments, the present disclosure provides stable oral palatable suspension formulations of an anti-spasmodic agent. In some embodiments, the formulations have advantages of accurate dose titration, exhibit excellent dose uniformity, re-dispersibility characteristics, ease of administration, and dosing flexibility. In some embodiments, the formulation of present disclosure is suitable for breast feeding infants and children below 3 years as it is devoid of alcohol and artificial sweeteners. In some embodiments, the present disclosure aims to deliver small volumes of appropriate dose for the targeted age group thereby providing the flexibility of dosing in the hands of the pediatricians.

In some embodiments, the formulation demonstrates physical and chemical stability throughout the shelf life of the product according to recommended long-term storage conditions. In some embodiments, the disclosure also provides methods for the preparation of the oral suspension formulations. In some embodiments, the disclosure also provides uses of the oral suspension formulation.

In some embodiments, the disclosure provides oral suspension dosage forms of Drotaverine that exhibit improved taste, aftertaste, and palatability. The term “taste” is used herein to refer to the sensation of flavor experienced when a subject’s tongue comes into contact with a dosage form. The term “aftertaste” is used herein to refer to the sensation of flavor experienced in the mouth after administration of a dosage form. For example, an aftertaste typically lasts well after administration of Drotaverine. The perm “palatability” is used herein to refer to the physical sensation of a dosage form when it is in a subject’s mouth, such as the texture of a dosage form. In some embodiments, the disclosed oral suspension dosage forms disclosed herein exhibit improved taste, aftertaste, and palatability compared to presently available Drotaverine suspensions.

To mask the highly bitter and lingering aftertaste of Drotaverine, various techniques were evaluated, including using ingredients such as flavors, sweeteners, amino acids, polymer coatings, gelatin, gelatinized starch, liposomes, lecithins or lecithin-like substances, surfactants, salts, or polymeric membranes and using conventional granulation, spray congealing with lipids, inclusion complexes with cyclodextrins, freeze-drying processes, multiple emulsions. However, the final product from these techniques did not result in the desired product performance parameters including taste masking and palatability. Ion-exchange resins were then evaluated further.

While some of the unpleasant taste of Drotaverine was masked by using ion-exchange technology, the resulting product did not provide acceptable palatability characteristics because the resulting product was too bland. Therefore, additional studies targeting granule size and ratio of the drug-resin complex were performed. A combination approach of ion-exchange resins along with a blend of excipients and flavors resulted in the palatable oral suspension formulations of the present disclosure. In some embodiments, the formulation of the present disclosure is safe and acceptable from the global regulatory perspective for neonates, infants, and children less than 3 years old.

Drotaverine HCl degrades extensively in alkaline medium, higher oxidative stress conditions, and in presence of light. Not only did ion-exchange complexation technology mask the bitter taste of Drotaverine, it also surprisingly and unexpectedly exhibited excellent chemical stability throughout shelf life of the suspension formulations. In some embodiments, the disclosed formulations employ very few excipients, all of which are completely safe for pediatric patients, economical, and readily available.

In some embodiments, the disclosed formulations provide quick release of Drotaverine to provide relief to targeted pediatric patient populations. In some embodiments, the disclosed formulations of present disclosure have no adverse effect on drug dissolution release and bioavailability despite use of ion-exchange resin technology. In some embodiments, the disclosed oral suspension provides a mechanism to deliver in small volumes of drug doses, which is useful in very young children and infants. Further, in some embodiments, the disclosed oral suspension exhibits excellent dose uniformity and re-dispersibility characteristics. In some embodiments, dose uniformity and re-dispersibility are measured using HPLC. Bottles containing the suspension product are shaken to form a uniform suspension, then a sample of the suspension is taken and analyzed by HPLC to measure the content uniformity of the suspension. In some embodiments, the disclosed formulations are based on easily scalable and cost-effective manufacturing processes.

In some embodiments, the present disclosure provides a pharmaceutical combination of an anti-spasmodic agent and one or more anti-flatulent agents along with one or more pharmaceutically acceptable excipients. In some embodiments, the present disclosure also provides methods for preparation of the pharmaceutical combination. in some embodiments, the present disclosure also provides uses of the pharmaceutical combination.

In some embodiments, the present disclosure relates to a fixed dose pharmaceutical formulation comprising Drotaverine HCl with simethicone or dimethicone and one or more pharmaceutically acceptable excipients.

The inventors of the present disclosure tried solubilizing Drotaverine HCl in a ratio of dispersion media containing sorbitol liquid, glycerin, and water ranging from 1:1:1 to 3:2:1, respectively. However, the drug re-precipitated on storage in the above dispersion media. To obtain a physically and chemically stable product with good shelf life, the present inventors resolved this precipitation of Drotaverine in the proposed dispersion media. In order to avoid the precipitation of Drotaverine, the present inventors added a stabilizing agent to the dispersion media. For this, various possible stabilizing agents were evaluated including water-soluble polymers which can suitably increase solubility of Drotaverine in the proposed dispersion media and hence stabilize the suspension formulation to prevent precipitation of the drug.

Certain exemplary water-soluble polymers include hydroxypropyl methyl celluloses (HPMC), polyvinylpyrrolidones, gelatin, and soluble starches. Among these water-soluble polymers, polyvinylpyrrolidone (Povidone) is preferred. As polyvinylpyrrolidone includes both soluble and insoluble grades, soluble grades were found to provide the best stability. Usually, soluble polyvinylpyrrolidone is synthesized by polymerization. Free radical polymerization in water uses hydrogen peroxide as an initiator. The polymerization reaction can be terminated at any time, which makes it possible to produce soluble polyvinylpyrrolidone of about any molecular weight.

Kollidon® is in the market as a brand name for polyvinylpyrrolidone, a Kollidon® family now is a set of common excipients based on polyvinylpyrrolidone for use in the pharmaceutical industry. They have a great variety of applications in an oral formulation; the functions of oral formulation encompass fast disintegration, sustain drug release, solubility, bioavailability enhancement. The examples of soluble grade of Kollidon® (Povidone) are Kollidon®12 PF, 17 PF, 25, 30, 90F, and Kollidon®VA64 (Copovidone).

The inventors of present disclosure surprisingly and unexpectedly found no precipitation issue in one of the initial experiments wherein low molecular weight Povidone grade Kollidon® PF 12 was used, even though the Povidone grades are usually used as tablet binders for wet granulation processes for solid oral dosage forms. Additional experiments were executed with different grades of Kollidon® (PF 12, 17, 25, 30 and 90) with the levels ranging from about 2% to about 8% in proposed dispersion media.

Based on the above experiments, the precipitation issue was resolved using Povidone (Kollidon® PF12) for proposed dispersion media for suspension. Several suspension products with different levels of sorbitol, glycerin, Povidone as a stabilizer, sucrose, suspending agents such as xanthan gum and sodium carboxymethylcellulose, flavoring agents, and Drotaverine HCl were prepared and analyzed. A direct mixing process using a stirrer and homogenizer was used to prepare the suspension. Even though, the inventors were able to achieve a physically stable suspension, the final product remained unpalatable because of the highly bitter taste of Drotaverine HCl. Though artificial sweeteners, such as aspartame, sodium saccharin, acesulfame K, and sucralose are available, these artificial sweeteners are not extensively studied in infants & children below 3 years of age. In some embodiments, the formulation of the present disclosure comprises a natural sweetener. In some embodiments, the natural sweetener comprises sucrose, sorbitol, or a combination there.

In addition to bitterness of the suspension, chemical stability issues were observed in the form of high impurity levels in the suspension product due to degradation of Drotaverine that was beyond the limits recommended by global regulatory guidelines.

In order to resolve the issue of bitterness, ion exchange resins were used for taste masking. Ion exchange resins are solid and suitably insoluble high molecular weight polyelectrolytes that can exchange their mobile ions of equal charge with surrounding media. An ion exchange resin is an insoluble matrix (or support structure) normally in the form of small (1 to 2 mm diameter) beads, usually white or yellowish, fabricated from an organic polymer substrate. The material has highly developed structure of surface pores which are sites that easily trap nd release ions. The trapping of ions takes place only with simultaneous releasing of other ions; thus, the process is called ion exchange. There are multiple different types of ion exchange resin which are fabricated to selectively prefer one or several different types of ions.

In some embodiments, the ion exchange resin comprises cross linked polyacrylic acid polymers or salts thereof, including Kyron grade polymers. In some embodiments, the Kyron grade polymer comprises Kyron 114 or Kyron 314 (Corel Pharma Chem, Ahmedabad). In some embodiments, the ion exchange resin comprises an Indion grade polymer. In some embodiments, the Indion grade polymer comprises Indion 204, Indion 234, or Indion 294 (Ion Exchange India Ltd., Mumbai).

A representation of the ion-exchange process showing the acid-base complexation formed from a positively charged drug ($D^+$) and a cation exchange resin ($RCOO^-$) is depicted below:

$$D^+ + RCOO^- \rightarrow RCOO\text{-}D \quad \text{(Formulation in mouth)}$$

$$RCOO\text{-}D + H^+ + Cl^- \rightarrow D^+ + RCOOH + Cl^- \quad \text{(Formulation in stomach)}$$

Ion exchange resins mask the taste of a drug because the resin-drug complexes that form elute little to no drug in the neutral pH of the mouth. Thus, the taste of the drug is masked in the mouth without interrupting the drug release profile in the stomach.

Several studies were undertaken in order to develop suitable Drotaverine drug-resin complex which can result in masking of bitterness and lingering after taste. The drug and suitable grade of ion-exchange resins were selected based on the initial studies, wherein, drug to polymer ratio was ranging from 1:1 to 1:8. Ion-exchange resins were initially mixed in water and stirred for sufficient time using suitable means. Thereafter, Drotaverine or salt thereof was added slowly in to resin mixture and stirred for sufficient time to obtain resinate. The resinate obtained was separated by filtration using suitable sieve. Thereafter, the filtered resin complex was washed until the filtrate obtained after washing was nearly free of unbound or free Drotaverine drug. The percentage of free Drotaverine drug unbound to resin should not exceed 2% w/w of the input drug at the start of complexation process; preferably less than 1% w/w. Thereafter, the drug-resin complex is either used directly for preparation of suspension or can be dried overnight at room temperature. The drying of drug-resin complex can be undertaken using suitable drying equipment, which may include but not limited to, tray dryer or fluidized bed dryer until target water content of less than 5.0% w/w is achieved. The dried drug-resin complex is tested for free Drotaverine drug. The free drug content should not be more than 2.0%.

The dried drug-resin complex was then used for formulation of oral suspension by using suitable additives which may include, suspending agents, sweetening agents, flavors, colorants, antioxidants, chelating agents, surfactants, wetting agents, antifoaming agents, pH modifiers, acidifiers, preservatives, solvents, or mixtures thereof.

In some embodiments, the oral suspension comprises a solvent. In some embodiments, the solvent is a sugar alcohol, a polyhydric alcohol, or a combination thereof. In some embodiments, the sugar alcohol is sorbitol. In some embodiments, the sorbitol is a 70% liquid dispersion. In some embodiments, the polyhydric alcohol is glycol, glycerin, or a combination thereof. In some embodiments the solvent is sorbitol (70% liquid) and glycerin with and the ratio of sorbitol (70% liquid):glycerin is 1:1 to 9:1. In some embodiments, the ratio of sorbitol (70%):glycerin is 2:1 to 8:1.

In some embodiments, the oral suspension comprises a suspending agent. In some embodiments, the suspending agent is sodium carboxymethylcellulose (Sod CMC), xanthan gum, or combinations thereof. In some embodiments the amount of suspending agent is in the range of 0.05% to 3.0% w/w. In some embodiments, the amount of suspending agent is in the range of 0.05%, to 2.0% w/w.

Sugar alcohols are fairly safe and the recommended intake of sugar alcohol is 10-15 grams per day. Suitable sugar alcohols include sorbitol which is used as a 70% liquid dispersion.

Suitable polyhydric alcohol include glycol, glycerin, and the likes. In some embodiments, the oral suspension comprises an acidifying agent, an acidifier, a pH modifier, or a combination thereof. In some embodiments, the acidifying agent, acidifier, or pH modifier is citric acid, fumaric acid, lactic acid, maleic acid, malic acid, tartaric acid, or a combination thereof.

In some embodiments, the oral suspension comprises an antioxidant. In some embodiments, the antioxidant is butylated hydroxyanisole (BHA), butylated hydroxytoluene (BHT), sodium metabisulfite, sodium thiosulfate, propyl gallate, ascorbic acid, glycine, cysteine, or combinations thereof. In some embodiments the amount of antioxidant is in the range of 0.05 to 4% w/w. In some embodiments, the amount of antioxidant is 0.1 to 3.0% w/w.

In some embodiments, the oral suspension comprises a wetting agent. In some embodiments, the wetting agent is a long alkyl chain sulfonate, long alkyl chain sulfate, quaternary ammonium salt, fatty alcohol, fatty acid ester, polyoxyethylene derivative of a fatty acid ester, or combinations thereof. In some embodiments, the long alkyl chain sulfate is sodium dodecylbenzene sulfonate, sodium lauryl sulfate, dialkyl sodium sulfosuccinate, or a combination thereof. In some embodiments, the fatty alcohol is a laurylester, cetylester, sterylester, glycerylester, or combination thereof. In some embodiments, the polyoxyethylene derivative is synthesized by the addition of an ethylene oxide via polymerization to obtain sorbitan fatty acid esters. These are nonionic hydrophilic surfactants commonly known as the Tweens or Polysorbates, e.g., polysorbate 20, 60, and 80.

In some embodiments, the oral suspension comprises a preservative. In some embodiments, the preservative is a parabens or sodium salt thereof. In some embodiments, the parabens is a methyl parabens, propyl parabens, or sodium salts thereof. In some embodiments, the preservative is a benzyl alcohol Thiomersal, or combination thereof.

In some embodiments, the oral suspension comprises a flavoring agent. In some embodiments, the flavoring agent is a natural flavor, natural fruit flavor, artificial flavor, artificial fruit flavor, flavor enhancer, or combination thereof. In some embodiments, the flavoring agent used is strawberry, cherry, orange, peppermint, black currant, banana, raspberry, red fruit, wild berry, caramel, or combination thereof.

Additionally, some of the flavors supplying companies also offer their special flavors which are usually named as Bitter masking flavors. They are usually a combination of sweeteners and flavors to mask the unpleasant taste of low to moderately bitter actives. In some embodiments, the oral suspension comprises an effervescent agent, which can be added to improve the mouth feel. In some embodiments, the effervescent agent is sodium bicarbonate, citric acid, or a combination thereof. In some embodiments, the flavoring agent or effervescent agent is used in addition to other taste masking techniques to achieve the target taste profile of the product.

In some embodiments, the oral suspension comprises a coloring agent. Coloring agents or colorants may be incorporated to provide an appealing color to the pharmaceutical formulation. In some embodiments, the coloring agent is deemed safe for human consumption by relevant governmental regulatory bodies and avoids chemical incompatibilities with other ingredients. In some embodiments, the coloring agent is sunset yellow FCF (known as FD&C yellow No. 6 and Tartrazine in the US) which is a synthetic lemon-yellow azo dye. It is also known as FD&C Yellow 5.

As an alternate manufacturing method according to some embodiments, drug resin complex in wet stage itself can be formulated directly as an oral suspension formulation using certain above-mentioned additives without drying of the drug-resin complex.

Based on extensive trials with different combinations, the drug-resin complex in the ratio of 1:2 to 1:6 was finalized and after drug-resin complexation and drying step, granule size of the drug-resin complex was finalized. In order to ensure smooth texture and palatability aspects, the dried drug-resin complex granules particle size was sufficiently reduced with appropriate milling parameters to ensure the final suspension product is free of grittiness and provide smooth feel while swallowing. Based on the development studies, in some embodiments, the appropriate granule size should be less than 50 mesh, ASTM (equivalent to around 300 microns), preferably 60 mesh, ASTM (equivalent to around 250 microns) or more preferably around 100 mesh, ASTM (equivalent to around 150 microns) was developed.

Once the desired particle size specifications of drug-resin complex were firmed up according to some embodiments, further formulation experiments were conducted for suspension formulations.

In some embodiments, the prepared drug-resin complex was employed for manufacturing suspension formulations.

The method of preparation of stable palatable suspension formulations of some embodiments of the present disclosure comprises the steps of:

1. Heating a quantity of water to an appropriate temperature and pH, followed by adding one or more preservatives and milled sucrose with continuous stirring until dissolved to obtain a solution.
2. Cooling down the solution obtained in step (1) to an appropriate temperature to obtain a cooled solution.
3. Adding one or more acidifiers and antioxidants into cooled solution of step (2) at a suitable stirring speed until dissolved to obtain a solution.
4. Adding one or more wetting agents into the solution of step (3) at an appropriate stirring speed for sufficient time to avoid undue frothing and until it disperses well to obtain a solution.
5. Adding a dispersion that has been obtained by soaking one or more suspending agents in a sufficient quantity of water before adding the one or more agents to the suspension for a sufficient time, preferably overnight, into the solution obtained in step (4) followed by addition of one or more stabilizers, stirring until they are dissolved to obtain a dispersion.

6. Sifting a drug-resin complex through an appropriate sieve followed by adding the drug-resin complex into the dispersion of step (5) and stirring for a sufficient time until it disperses uniformly to obtain a bulk suspension.
7. Adding the anti-flatulent agent, sweetener, and coloring agent into the bulk suspension of step (6) at an appropriate stirring speed for a sufficient time to obtain a suspension product.
8. Adjusting the volume of the suspension product of step (7) with a quantity of water to obtain a final suspension product.

In some embodiments, the final suspension product is filled into suitable containers using a suitable filling machine. In some embodiments, the filled containers may be sealed and optionally sterilized prior to or after the sealing.

In some embodiments, the disclosure provides a pharmaceutical combination comprising simethicone, dimethicone, or a mixture thereof, with Drotaverine or a salt thereof.

In some embodiments, the disclosed formulations achieved an improved taste profile using a drug-resin complex in combination with flavorants, sweeteners, stabilizers, and other additives. The disclosed formulations were also evaluated for chemical stability using accelerated stability conditions. Even though the drug-resin complexation technology was initially evaluated with the objective of taste masking, the inventors of the present disclosure surprisingly observed in some embodiments a significant improvement in the chemical stability of the suspension product compared to suspension products made without using an ion-exchange resin. Even the addition of antioxidants alone did not provide the stable product unless ion-exchange resins were used.

The observed impurity levels in the resulting suspension product was within target limits for impurities per the guidelines from the International Council for Harmonization of Technical Requirements for Pharmaceuticals for Human Use (ICH).

The terms "stable," "stability," or "stabilized" mean the dosage form is able to maintain a product performance test parameters such as an ingredient amount, a related substance amount, without significant changes from the initial levels.

The term "significant change" means a change of 5% or more from the initial result. For example, if the initial amount of an ingredient is 98%, then a significant change would be an amount of 93% or less of that ingredient. If the product is stable under accelerated conditions (40° C./75% RH) for 6 months without significant change, then it can be assigned a shelf life of at least 2 years or 24 months.

In some embodiments, the oral suspension is stable under long-term storage conditions for at least three months. In some embodiments, the oral suspension is stable under long-term storage conditions for at least six months. In some embodiments, long term storage conditions comprise 25-30° C. at 60-75% RH. In some embodiments, long term storage conditions comprise 15-30° C. at 60-75% RH In some embodiments, the flavoring agents used in the present disclosure were of type and amount desired to enhance the palatability of the formulation. Exemplary flavoring agents that may be used in the present disclosure include natural flavors, natural fruit flavors, artificial flavors, artificial fruit flavors, flavor enhancers, or mixtures thereof. Exemplary natural flavors, artificial flavors or mixtures thereof include mint (such as peppermint or spearmint), and menthol. Exemplary natural fruit flavors, artificial fruit flavors, or mixtures thereof include cherry, grape, Berry (such as strawberry, raspberry, blackberry, blueberry, cranberry), orange-blood, melon, banana, citrus, and vanilla. Although flavoring agents are generally provided as a minor component of the taste masking composition in amounts effective to provide a palatable flavor to the suspension formulation, the addition of at least one flavoring agent is preferred in some embodiments, and more preferably, more than one flavoring agent may be employed in some embodiments.

In some embodiments, coloring agents or colorants may be incorporated to provide an appealing color to the suspension formulation. Suitable coloring agents are well known to those skilled in the art and are those that are deemed safe for human consumption by relevant governmental regulatory bodies and that avoid chemical incompatibilities with other ingredients.

In some embodiments, the disclosed oral suspension formulations of present disclosure exhibit faster drug release in comparison to currently marketed oral suspension product.

As representative suitable formulations consistent with the objects, features and advantages of the present disclosure, the following non-limiting examples are provided.

Example 1: Method for Preparation of Drug-Resin Complex

Ion-exchange resins were initially mixed in about 4 to 8 volumes of water and stirred for about 30 to 45 minutes using a mechanical stirrer at 45-65 degrees Celsius and 5.5-7.0 pH. Thereafter, Drotaverine HCl was added slowly into the resin mixture and stirred for at least 2 to 4 hours to obtain the drug-resin complex. The drug-resin complex was prepared by using drug and resin in ratio of 1:2 to 1:6. The drug-resin complex obtained was separated by filtration using a Sieve #80 (ASTM) to obtain filtered resin complex. Thereafter, the filtered drug-resin complex was washed with water until the filtrate obtained after washing was nearly free of unbound Drotaverine drug.

The drug-resin complex that was obtained and used directly for preparation of the suspension. In another experiment, the drug-resin complex was dried overnight at room temperature. The drug-resin complex was dried until the target water content of less than 5.0% w/w was achieved. The dried drug-resin complex is tested for free Drotaverine drug. The free drug content should not be more than 2.0%.

The dried drug-resin complex can either be used immediately for formulation of oral suspension by using suitable additives or can be stored for later use. Suitable additives, including but not limited to sweetening agents, flavors, colorants, antioxidants, chelating agents, surfactants, wetting agents, antifoaming agents, pH modifiers, acidifiers, preservatives, co solvents, and mixtures thereof were added. See Examples 3 11 below.

After the drug-resin complexation and optional drying step, the drug-resin complex was milled until the target granule size of less than 50 mesh, American Standard Test Sieve Series (ASTM) (equivalent to around 300 microns), 60 mesh, ASTM (equivalent to around 250 microns), or around 100 mesh, ASTM (equivalent to around 150 microns) was achieved.

Example 2: Method for Preparation of Suspension Formulations from Drug-Resin Complex The drug-resin complex prepared in Example 1 was employed for manufacturing the suspension formulation product.

In some embodiments, the method of preparation of stable palatable suspension formulation of present disclosure comprises steps of:

1. Heating an amount of water that would be about 30% of the target batch size to 45-65 degrees Celsius and 5.5-7.0 pH in initial phase, followed by adding methyl paraben, propyl paraben, and milled sucrose at continuous stirring until dissolved to obtain a solution.
2. Cooling down the solution obtained in step (1) to 25-40 degrees Celsius to obtain a cooled solution.
3. Adding citric acid and sodium metabisulphite into cooled solution of step (2) with citric acid added first, followed by sodium metabisulphite, at 500-1000 rpm until dissolved to obtain a solution.
4. Adding polysorbate 80 into solution of step (3) at appropriate 300-500 rpm for 15-20 minutes to avoid undue frothing and until it disperses well to obtain a solution.
5. Adding a dispersion obtained by soaking xanthan gum or sodium CMC in an amount of water that would be about 1-2% of the target batch size before adding them in major bulk of suspension for sufficient time, preferably overnight, into the solution obtained in step (4) followed by addition of povidone under stirring until dissolved to obtain bulk solution.
6. Sifting drug-resin complex through Sieve #80 (ASTM) followed by adding it into bulk solution of step (5) and stirring for 20-30 minutes until it disperses uniformly to obtain bulk suspension.
7. Adding simethicone, sorbitol, a colorant, and a flavorant into bulk suspension of step (6) at 1000-2000 rpm for 20-30 minutes to obtain a suspension product.
8. Adjusting the volume of suspension product of step (7) with an amount of water that would be about 5-10% of the target batch size to obtain the final suspension product.

In some embodiments, the final suspension product is filled into bottles of about 100 to 200 mL capacity by hand, however, a semi-automatic or fully automatic filling machine may be used. In some embodiments, the filled bottles are sealed using an ROPP sealing machine.

The following exemplary formulations comprising Drotaverine were prepared by preparation methods described above in Examples 1 and 2 by employing varying ratio of drug and resin in the drug-resin complex.

Example 3: An Exemplary Formulation Comprising Drotaverine was Prepared by Employing Drug-Resin Complex Having Drotaverine and Resin in Ratio of 1:2.5

TABLE 1

Formulation comprising Drotaverine-resin complex (1:2.5)

| Ingredients | mg/mL |
|---|---|
| Methyl paraben Sodium | 1.00 |
| Propyl paraben Sodium | 0.20 |
| Citric acid | 1.20 |
| Sucrose | 450.00 |
| Xanthan gum | 1.50 |
| Kollidon 12PF | 8.00 |
| Tween 80 | 1.80 |
| Drotaverine-Kyron 114 resin complex (1:2.5) | 69.65 |
| Simethicone | 20.00 |
| Tartrazine supra | 0.00 |

TABLE 1-continued

Formulation comprising Drotaverine-resin complex (1:2.5)

| Ingredients | mg/mL |
|---|---|
| Menthol | 0.01 |
| Berry Flavour | 2.00 |
| Sorbitol 70% | 120.00 |
| Glycerin | 70.00 |
| Water | 610.00 |

Example 4: An Exemplary Formulation Comprising Drotaverine was Prepared by Employing Drug-Resin Complex Having Drotaverine and Resin in Ratio of 1:3

TABLE 2

Formulation comprising Drotaverine-resin complex (1:3)

| Ingredients | mg/mL |
|---|---|
| Propylene glycol | 200.00 |
| Methyl paraben | 1.00 |
| Propyl Paraben | 0.20 |
| Citric acid | 1.20 |
| Sucrose | 600.00 |
| Sodium CMC | 6.00 |
| Kollidon 12PF | 5.00 |
| Ascorbic acid | 20.00 |
| Drotaverine-Indion resin complex (1:3) | 76.90 |
| Simethicone | 40.0 |
| Tartrazine supra | 0.00 |
| Menthol | 0.01 |
| Mango Flavour | 2.00 |
| Sorbitol 70% | 160.00 |
| Glycerin | 50.00 |
| Water | 340.00 |

Example 5: An Exemplary Formulation Comprising Drotaverine was Prepared by Employing Drug-Resin Complex Having Drotaverine and Resin in Ratio of 1:4

TABLE 3

Formulation comprising Drotaverine-resin complex (1:4)

| Ingredients | mg/mL |
|---|---|
| Methyl paraben sodium | 1.00 |
| Propyl Paraben Sodium | 0.20 |
| Citric acid | 1.20 |
| Sucrose | 360.00 |
| Sodium CMC | 4.00 |
| Kollidon 12PF | 5.00 |
| Ascorbic acid | 20.00 |
| Tween 80 | 1.80 |
| Drotaverine-Kyron resin complex (1:4) | 100.00 |
| Simethicone | 20.00 |
| Tartrazine supra | 0.00 |
| Menthol | 0.01 |
| Mango Flavour | 2.00 |
| Sorbitol 70% | 140.00 |
| Glycerin | 50.00 |
| Water | 610.00 |

Example 6: An Exemplary Formulation of Drotaverine was Prepared by Employing Drug-Resin Complex Having Drotaverine and Resin in Ratio of 1:4

TABLE 4

Formulation comprising Drotaverine-resin complex (1:4)

| Ingredients | mg/mL |
|---|---|
| Methyl paraben Sodium | 1.00 |
| Propyl Paraben Sodium | 0.20 |
| Citric acid | 1.20 |
| Sucrose | 300.00 |
| Sodium CMC | 4.00 |
| Kollidone 12PF | 5.00 |
| Ascorbic acid | 20.00 |
| Tween 80 | 1.80 |
| Drotaverine-Indion resin complex (1:4) | 50.00 |
| Simethicone | 20.00 |
| Tartrazine supra | 0.00 |
| Menthol | 0.01 |
| Mango Flavour | 2.00 |
| Sorbitol 70% | 140.00 |
| Glycerin | 50.00 |
| Water | 610.00 |

Example 7: An Exemplary Formulation of Drotaverine was Prepared by Employing Drug-Resin Complex Having Drotaverine and Resin in Ratio of 1:4

TABLE 5

Formulation comprising Drotaverine-resin complex (1:4)

| Ingredients | mg/mL |
|---|---|
| Methyl paraben Sodium | 1.00 |
| Propyl Paraben Sodium | 0.20 |
| Citric acid | 1.20 |
| Sucrose | 350.00 |
| Sodium CMC | 4.00 |
| Kollidon 12PF | 5.00 |
| Ascorbic acid | 20.00 |
| Tween 80 | 1.80 |
| Drotaverine-Kyron resin complex (1:4) | 75.00 |
| Simethicone | 20.00 |
| Tartrazine supra | 0.00 |
| Menthol | 0.01 |
| Mango Flavour | 2.00 |
| Sorbitol 70% | 150.00 |
| Glycerin | 50.00 |
| Water | 640.00 |

Example 8: An Exemplary Formulation of Drotaverine was Prepared by Employing Drug-Resin Complex Having Drotaverine and Resin in Ratio of 1:5

TABLE 6

Formulation comprising Drotaverine-resin complex (1:5)

| Ingredients | mg/mL |
|---|---|
| Methyl paraben | 1.00 |
| Propyl Paraben | 0.20 |
| Citric acid | 1.20 |
| BHA | 0.80 |
| Sucrose | 400.00 |
| Sodium CMC | 3.00 |
| Kollidon 12PF | 3.00 |
| Sodium metabisulfite | 1.00 |
| Ascorbic acid | 2.0 |
| Tween 80 | 1.80 |
| Drotaverine-Kyron resin complex (1:5) | 125.00 |
| Simethicone | 40.00 |
| Tartrazine supra | 0.00 |
| Menthol | 0.01 |
| Strawberry Flavour | 4.00 |
| Sorbitol 70% | 130.00 |
| Glycerin | 20.00 |
| Water | 400.00 |

Example 9: An Exemplary Formulation of Drotaverine was Prepared by Employing Drug-Resin Complex Having Drotaverine and Resin in Ratio of 1:2

TABLE 7

Formulation comprising Drotaverine-resin complex (1:2)

| Ingredients | mg/mL |
|---|---|
| Methyl paraben | 1.00 |
| Propyl paraben Sodium | 0.20 |
| Citric Acid | 1.20 |
| BHA | 2.00 |
| Sucrose | 500.00 |
| Xanthan gum | 1.50 |
| Kollidon 12PF | 6.00 |
| Sodium metabisulfite | 1.00 |
| Ascorbic acid | 2.00 |
| Tween 80 | 1.80 |
| Drotaverine-Indion resin complex (1:2) | 50.00 |
| Tartrazine supra | 0.00 |
| Menthol | 0.01 |
| Raspberry Flavour | 2.00 |
| Sorbitol 70% | 100.00 |
| Glycerin | 40.00 |
| Water | 615.00 |

Example 10: An Exemplary Formulation of Drotaverine was Prepared by Employing Drug-Resin Complex Having Drotaverine and Resin in Ratio of 1:3

TABLE 8

Formulation comprising Drotaverine-resin complex (1:3)

| Ingredients | mg/mL |
|---|---|
| Methyl paraben | 1.50 |
| Propyl paraben | 0.30 |
| Citric Acid | 1.80 |
| BHA | 2.50 |
| Sucrose | 600.00 |
| Xanthan gum | 1.50 |
| Kollidon 12PF | 8.00 |

TABLE 8-continued

| Formulation comprising Drotaverine-resin complex (1:3) | |
|---|---|
| Ingredients | mg/mL |
| Sodium metabisulfite | 1.50 |
| Tween 80 | 1.80 |
| Drotaverine-Indion resin complex (1:3) | 120.00 |
| Tartrazine supra | 0.02 |
| Menthol | 0.01 |
| Mint Flavour | 2.00 |
| Sorbitol 70% | 140.00 |
| Glycerin | 40.00 |
| Water | 412.00 |

Example 11: An Exemplary Formulation of Drotaverine was Prepared by Employing Drug-Resin Complex Having Drotaverine and Resin in Ratio of 1:4

TABLE 9

| Formulation comprising Drotaverine-resin complex (1:4) | |
|---|---|
| Ingredients | mg/mL |
| Methyl paraben | 0.25 |
| Propyl Paraben | 0.05 |
| Citric acid | 0.30 |
| Sucrose | 75.00 |
| Xanthan Gum | 1.00 |
| Kollidon 12PF | 1.25 |
| Ascorbic acid | 5.00 |
| Tween 80 | 0.45 |
| Drotaverine-Indion resin complex (1:4) | 12.50 |
| Simethicone | 5.00 |
| Tartrazine supra | 0.02 |
| Menthol | 0.01 |
| Mango Flavour | 1.00 |
| Sorbitol 70% | 40.00 |
| Glycerin | 20.00 |
| Water | 160.00 |

Example 12

The oral suspension (20 mg/mL) formulation illustrated in Examples 3 to 11. One of the representative formulations (Example 8) was evaluated for in vitro drug dissolution study according to the test conditions below and demonstrated faster drug release compared to a currently marketed 20 mg/5 mL oral suspension product. Hence, the disclosed suspension according to these examples show quick drug release, suggesting they will lead to faster pain relief than the currently available oral suspension product.

TABLE 10

Comparative drug dissolution data for Drotaverine oral suspension of commercially available suspension vs. present disclosure.

| | Dissolution Condition | |
|---|---|---|
| | Apparatus | Paddle |
| | RPM | 40 |
| | Sample withdrawn | 10 |
| | Media Volume | 750 |
| | Dissolution Media | 0.1N HCl |

| | % Drug dissolved | |
|---|---|---|
| Time (in minutes) | Drotaverine oral suspension 20 mg/5 mL (comparative) | Drotaverine suspension 20 mg/mL (Present disclosure) |
| 5 | 39 | 51-71 |
| 10 | 78 | 80-94 |
| 15 | 91 | 92-99 |

Example 13: Stability Data

The disclosed suspension formulations of Examples listed demonstrate good chemical and physical stability in view of the accelerated stability data using ICH guidelines (40° C.±2° C./75% RH±5% RH). The observed impurity levels in the resulting products were within target limits for impurities under the ICH guideline. The Accelerated stability data of one of the representative formulations with Drug-Resin complex is given below (Table-11) in comparison to a formulation made without resin complex technology (Table-12):

TABLE-11

| | | Formulation with Drug-Kyron Resin complex | | | | |
|---|---|---|---|---|---|---|
| Test | | Initial | ACC/1M | ACC/2M | ACC/3M | ACC/6M |
| Description | | Light yellow colored viscous suspension | Light yellow colored viscous suspension | Light yellow colored viscous suspension | Light yellow colored viscous suspension | Light yellow colored viscous suspension |
| pH | | 3.95 | 3.82 | 3.87 | 3.97 | 3.81 |
| Simethecone Assay | | 40.32 mg/ml | 39.86 mg/ml | 39.21 mg/ml | 39.22 mg/ml | 39.12 mg/ml |
| Drotaverine Assay | | 21.92 mg/ml | 21.56 mg/ml | 20.71 mg/ml | 20.23 mg/ml | 20.31 mg/ml |
| RS | Drotaverladine | 0.20 | 0.24 | 0.21 | 0.22 | 0.21 |
| | Highest unknown | 0.05 | 0.04 | 0.06 | 0.07 | 0.19 |
| | Total Impurities | 0.33 | 0.38 | 0.26 | 0.23 | 0.60 |

TABLE 12

| Test | | Formulation Without Drug-Resin complex | | | | |
|---|---|---|---|---|---|---|
| | | Initial | ACC/1 M | ACC/2 M | ACC/3 M | ACC/6 M |
| Description | | Light yellow colored viscous suspension | Light yellow colored viscous suspension | Light yellow colored viscous suspension | Light yellow colored viscous suspension | Light yellow colored viscous suspension |
| pH | | 3.95 | 3.91 | 3.89 | 3.87 | 3.81 |
| Simethecone Assay | | 40..2 mg/ml | 38.1 mg/ml | 37.4 mg/ml | 37.02 mg/ml | 36.4 mg/ml |
| Drotaverine Assay | | 20.10 mg/ml | 19.41 mg/ml | 19..02 mg/ml | 18.67 mg/ml | 17.41 mg/ml |
| RS | Drotaverladine | 0.41 | 0.75 | 0.93 | 1.51 | 2.76 |
| | Highest unknown | 0.23 | 0.52 | 0.83 | 1.03 | 1.37 |
| | Total Impurities | 0.74 | 2.65 | 4.23 | 6.92 | 11.98 |

As evident from the Table-11 and 12 data, the drug-resin formulation has surprisingly and unexpectedly improved the stability of Drotaverine. The drug-resin formulation showed low impurity levels in the accelerated stability studies.

Although the subject matter has been described herein with reference to certain preferred embodiments thereof, other embodiments are possible. For illustrative purpose, some embodiments of the disclosure are in oral liquid forms such as suspensions, solutions, emulsions, elixir, linctus, mixtures and comprises Drotaverine or salt thereof as the anti-spasmodic agent. Further, for illustrative purpose, some embodiments of the present disclosure are suitable for neonates, infants and children below 6 years of age. However, those skilled in the art would appreciate that scope of the disclosure extends to combinations and formulations suitable for other age groups, in other forms of oral administration and can comprise other anti-spasmodic agents known in the field of art.

What is claimed:

1. An oral suspension comprising Drotaverine or a salt thereof, wherein the Drotaverine or salt thereof is in a concentration of greater than 4 mg/ml.

2. The oral suspension of claim 1, wherein the oral suspension comprises a Drotaverine-resin complex, wherein the ratio of Drotaverine to resin is 1:2 to 1:6.

3. The oral suspension of claim 2 wherein the Drotaverine-resin complex comprises granules, wherein the size of the granules are in the range of 300 microns to 150 microns.

4. The oral suspension of claim 2, wherein the resin is selected from at least one cross linked polyacrylic acid polymer.

5. The oral suspension of claim 1, wherein the oral suspension further comprises an anti-flatulent agent.

6. The oral suspension of claim 5, wherein the anti-flatulent agent is simethicone or activated dimethicone.

7. The liquid oral suspension of claim 1, wherein the Drotaverine is hydrochloride.

8. The oral suspension of claim 1, wherein the oral suspension comprises 5-30 mg/ml Drotaverine or salt thereof.

9. The oral suspension of claim 6, wherein the oral suspension comprises 10-80 mg/ml simethicone or activated dimethicone.

10. The oral suspension of claim 1, wherein the oral suspension comprises a water-soluble polymer.

11. The oral suspension of claim 1, wherein the suspension comprises a solvent, wherein the solvent comprises a sugar alcohol, a polyhydric alcohol, or a combination thereof.

12. The oral suspension of claim 11 wherein the solvent comprises sorbitol (70% liquid) and a glycerin in a ratio of 1:1 to 9:1.

13. The oral suspension of claim 1, wherein the suspension comprises a suspending agent, wherein the suspending agent comprises sodium carboxymethylcellulose (Sod CMC), xanthan gum, or a combination thereof.

14. The oral suspension of claim 13, wherein the suspending agent is in an amount of 0.05% to 3.0% w/w.

15. The oral suspension of claim 1, wherein the oral suspension comprises a sweetener.

16. The oral suspension of claim 1, wherein the oral suspension comprises a flavorant, a colorant, an antioxidant, a chelating agent, a surfactant, a wetting agent, a pH modifier, an acidifier, a preservative, a solvent, or a combination thereof.

17. The oral suspension of claim 16, wherein the antioxidant is in an amount of 0.05% to 4% w/w.

18. The oral suspension of claim 17, wherein the antioxidant is in an amount of 0.1% to 3.0% w/w.

19. An oral suspension comprising Drotaverine hydrochloride, a cross linked polyacrylic acid polymer, Simethicone, Xanthan gum, polyvinylpyrrolidone, Sucrose, Citric acid, Tween-80, Sodium metabisulphite, Sorbitol 70%, glycerin, Methyl Paraben, Propyl Paraben, and a flavoring agent, wherein the Drotaverine hydrochloride and cross linked polyacrylic acid polymer comprise a drug-resin complex, and wherein the Drotaverine hydrochloride and cross linked polyacrylic acid polymer are in a 1:3 ratio.

20. The oral dosage form of claim 1, wherein the oral suspension is stable for six months when stored at 40° C. and 75% RH as accelerated storage conditions.

21. The oral suspension of claim 1, wherein the oral suspension is stable for 2 years when stored at 25-30° C. and 60-75% RH as long-term storage conditions.

22. The oral suspension of claim 1, wherein the oral suspension exhibits improved taste.

23. The oral suspension of claim 1, wherein the oral suspension exhibits improved aftertaste.

24. The oral suspension of claim 1, wherein the oral suspension exhibits improved palatability.

25. A method of preparing an oral suspension of Drotaverine or salt thereof comprising:

a. heating a quantity of water and adding at least one preservative and milled sucrose, stirring the resulting mixture continuously until dissolved to obtain a solution;

b. cooling the solution to obtain a cooled solution;

c. adding at least one acidifier and at least one antioxidant into the cooled solution until dissolved to obtain a solution;

d. adding at least one wetting agent into the solution until dissolved to obtain a solution;

e. adding at least one stabilizer and a dispersion that has been obtained by soaking at least one suspending agent in water, until dissolved to obtain a bulk solution;

f. sifting a drug-resin complex comprising Drotaverine or a salt thereof through a sieve, adding the bulk solution obtained in step (e), and stirring until dissolved to obtain a bulk suspension; and g. adding a quantity of water to the bulk suspension to obtain a suspension of Drotaverine or a salt thereof.

26. The method of claim 25, wherein the method comprises adding simethicone or activated dimethicone with Drotaverine in step (f).

27. A method of treating abdominal pain comprising administering to a subject in need thereof an oral suspension comprising Drotaverine or a salt thereof and Simethicone, wherein the oral suspension comprises the oral suspension of claim 1.

* * * * *